United States Patent
Sablone et al.

(10) Patent No.: US 12,193,918 B2
(45) Date of Patent: Jan. 14, 2025

(54) ADAPTIVE CARRIER UNIT AND TRANSFER SYSTEM

(71) Applicant: Fameccanica.Data S.p.A., San Giovanni Teatino (IT)

(72) Inventors: Gabriele Sablone, San Giovanni Teatino (IT); Massimiliano Rossetti, San Giovanni Teatino (IT); Carlo Di Sabatino, San Giovanni Teatino (IT); Marco Delli Rocioli, San Giovanni Teatino (IT)

(73) Assignee: Fameccanica.Data S.p.A., San Giovanni Teatino Chieti (IT)

( * ) Notice: Subject to any disclaimer, the term of this patent is extended or adjusted under 35 U.S.C. 154(b) by 37 days.

(21) Appl. No.: 17/737,171

(22) Filed: May 5, 2022

(65) Prior Publication Data
US 2022/0362066 A1 Nov. 17, 2022

(30) Foreign Application Priority Data
May 11, 2021 (EP) .................................... 21173193

(51) Int. Cl.
*A61F 13/15* (2006.01)
*B65G 47/86* (2006.01)

(52) U.S. Cl.
CPC ...... *A61F 13/15764* (2013.01); *B65G 47/847* (2013.01)

(58) Field of Classification Search
CPC .................... A61F 13/15764; B65G 47/847
USPC .......................................................... 53/568
See application file for complete search history.

(56) References Cited

U.S. PATENT DOCUMENTS

| 5,772,391 A * | 6/1998 | Sjogren | B65H 29/003 |
| | | | 198/470.1 |
| 7,475,771 B2 * | 1/2009 | Schmetzer | B65H 31/28 |
| | | | 198/803.1 |
| 2015/0136564 A1 * | 5/2015 | Hurni | B65B 57/16 |
| | | | 198/418 |

(Continued)

FOREIGN PATENT DOCUMENTS

| CN | 104603012 A | 5/2015 |
| CN | 105712047 A | 6/2016 |

(Continued)

OTHER PUBLICATIONS

European Search Report dated Oct. 18, 2021. 10 pages.
Chinese Office Action issued on May 20, 2024 in the parallel Chinese case. 7 pages.

*Primary Examiner* — Robert F Long
*Assistant Examiner* — Xavier A Madison
(74) *Attorney, Agent, or Firm* — RMCK Law Group PLC (57) ABSTRACT

A carrier unit for a transfer system having a transfer path includes a first carrier and a second carrier, the first and the second carriers being engageable to the transfer path and configured for negotiating the transfer path, wherein the first carrier is coupled to a first gripper configured for cooperating with a second gripper coupled to the second carrier to define a socket for holding one or more products, the socket having a socket geometry determined by a relative position of the first gripper with respect to the second gripper. Each carrier unit includes an angle control device configured to maintain the socket geometry upon negotiation of the transfer path by the carrier unit.

14 Claims, 8 Drawing Sheets

(56) References Cited

U.S. PATENT DOCUMENTS

2016/0176659 A1\* 6/2016 Aumann ................ B65G 54/02
198/619
2019/0367297 A1 12/2019 Hartung et al.

FOREIGN PATENT DOCUMENTS

| EP | 2741979 A1 | 6/2014 |
| EP | 3744649 A1 | 12/2020 |
| WO | 2020030836 A1 | 2/2020 |

\* cited by examiner fig. 2 fig. 1 fig.5 fig.8 fig.9 fig.10 fig.11 fig.12

ADAPTIVE CARRIER UNIT AND TRANSFER SYSTEM

CROSS-REFERENCE TO RELATED APPLICATION

This application claims priority to European Patent Application No. 21173193.0 filed May 11, 2021. The disclosure of the above application is incorporated herein by reference in its entirety.

FIELD OF THE INVENTION

The present invention relates to transfer systems, particularly transfer systems for products such as diapers or sanitary napkins which are intended to be packaged as stacks of products, and transferred in stacked or packed fashion as well.

PRIOR ART

Transfer systems for the above-mentioned products generally involve a transfer path featuring one or more bends or changes of direction. This path is conveniently negotiated by means of so-called "flexible carriers" such as ACOPOSTrak® carriers, which allow negotiation of complex paths through multiple, selectable, tracks and related junctions. Embedded in the tracks are driving means such as, for instance, linear motors (stator units).

Flexible carriers of this type, as well known in the art, are configured to engage a driving track on either side (left/right) thereof. Change of track is usually accommodated by changing the engagement side of the carrier, whereby a carrier moving—for instance—along a first track with left side out, right side in (facing the track) may accomplish track change to a second track at a junction by simply switching the engagement side from left to right, hence moving along the second track left side in, right side out.

While allowing exceptional flexibility, this feature also comes with a first major limit: any accessory, implement, end effector, payload, etc. mounted on the carrier must be positioned on top of the carrier itself to avoid interfering at the sides of the carrier, which would prevent engagement with a driving track.

A second major limit of such flexible carriers is the need to avoid disruption of the engagement with the driving track—typically achieved thanks to weak magnetic attraction—by inertial forces, which generally results in limitations to the process speed of the carriers and/or in the need for use of twin (split) grippers, i.e. pair-wise arranged grippers rigidly mounted on pairs of carriers.

Figure 1:
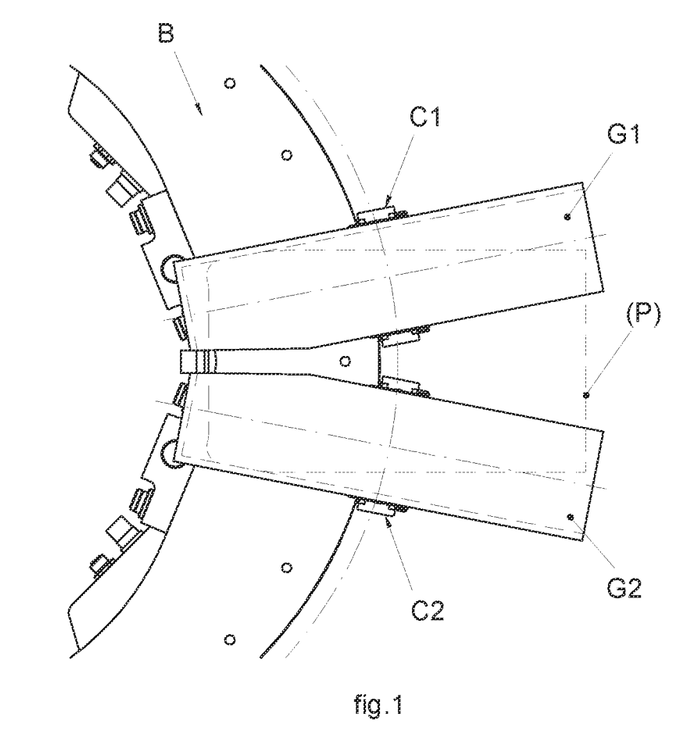
FIGS. 1 and 2 are representative of prior art transfer systems.
Figure 2:
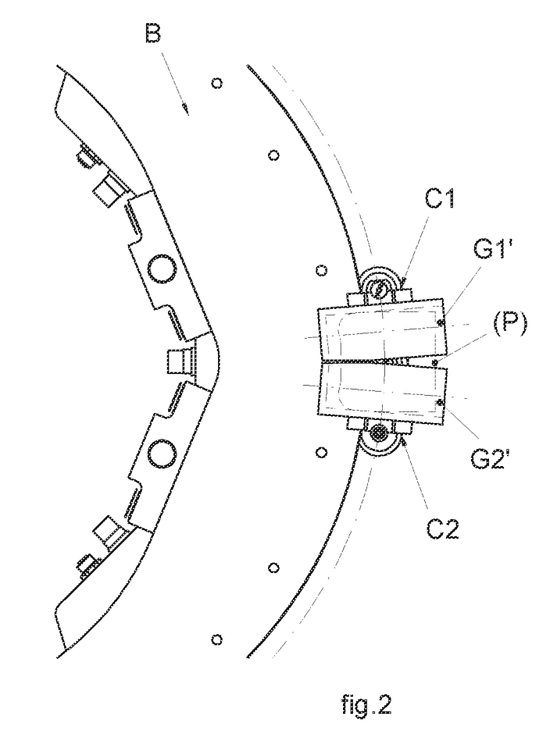

The first mentioned solution (reduction of process speeds) is largely unacceptable as it affects further processing stages. The second mentioned solution (pair-wise grippers) turns out to be effective only when negotiating rectilinear portions of the tracks, as negotiating a bend results in a change in the overall geometry of the gripping socket defined by the two grippers on the carriers. Reference is made, in this regard, to FIGS. 1 and 2 which show a prior art transfer system featuring flexible carriers, and particularly a bend portion B of the driving track. Engaged on the driving track are a first and a second carriers C1, C2 each featuring a gripper G1, G2 (FIG. 1, large products) or G1', G2' (FIG. 2, small products) mounted thereon and located at the bend portion B.

FIGS. 1 and 2 clearly show that the twin grippers require adaptation based on the product dimension (grippers G1, G2 are used for large products, while grippers G1', G2' are used for small products), but also—most notably—that the interference conditions with the products varies through the bend B due to dependency thereof from the radius of curvature thereof, and based on the product dimension (the rectangular outline referred to as (P) in FIGS. 1 and 2 is representative of the product dimension—when undeformed). More specifically, the smaller the radius, the larger the variation in the interference conditions, and the larger the product (and the grippers), the larger the variation of interference conditions.

This is clearly unacceptable, as it may ultimately result in the need for reducing processing speeds due to varied interference conditions, which may turn out to be insufficient to counter centrifugal forces when negotiating the bend.

OBJECT OF THE INVENTION

The object of the invention is to overcome the technical problems discussed in the foregoing.

Specifically, the object of the invention is to provide a transfer system which is easily adaptable to products of different dimensions, and which is essentially unaffected by bends or changes of directions in the path to be negotiated as far as the interference conditions with the products is concerned.

SUMMARY OF THE INVENTION

The object of the invention is achieved by a carrier unit and a transfer system having the features forming the subject of the appended claims, which form an integral part of the technical disclosure herein provided in relation to the invention.

BRIEF DESCRIPTION OF THE FIGURES

Further features and advantages of the invention will become apparent from the following description with reference to the annexed figures, provided purely by way of non limiting example, wherein:

FIG. 3 is a front, elevational view of the transfer system of the invention, while

DETAILED DESCRIPTION

Figure 3:
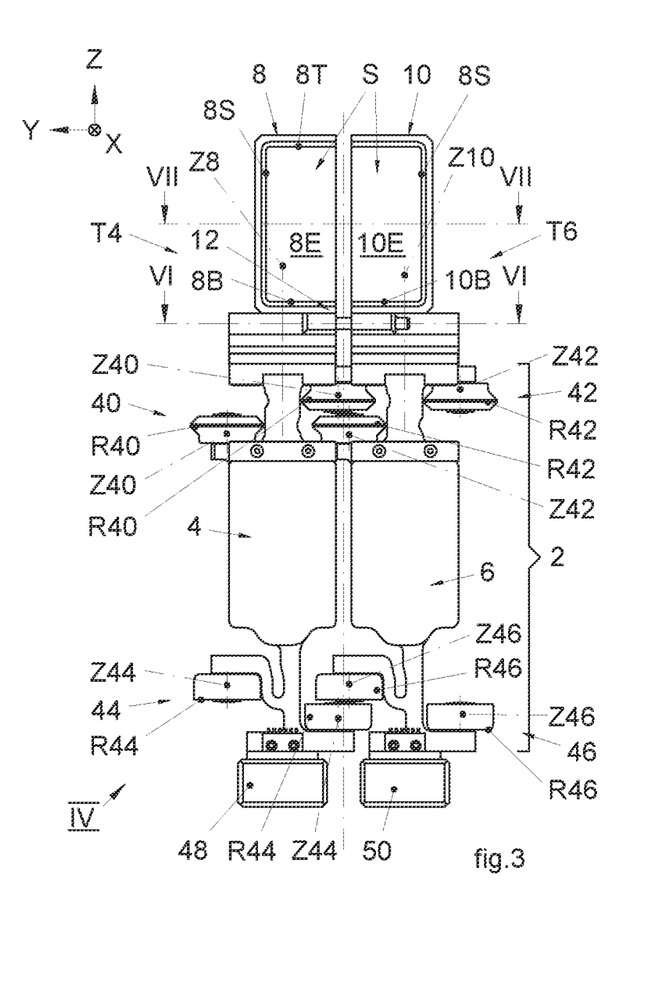
Figure 4:
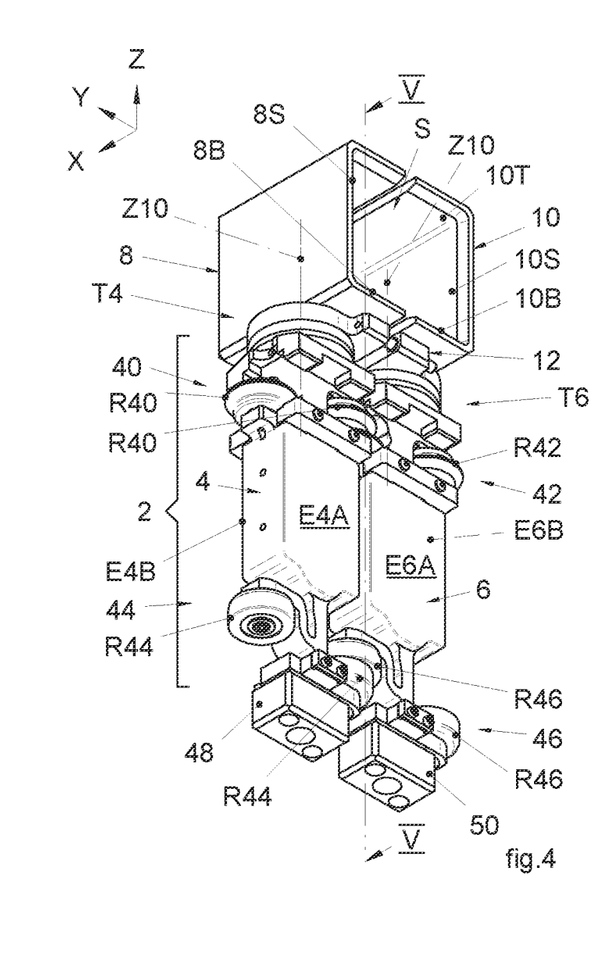
FIG. 4 is a perspective view according to pointer IV in FIG. 3.
Figure 5:
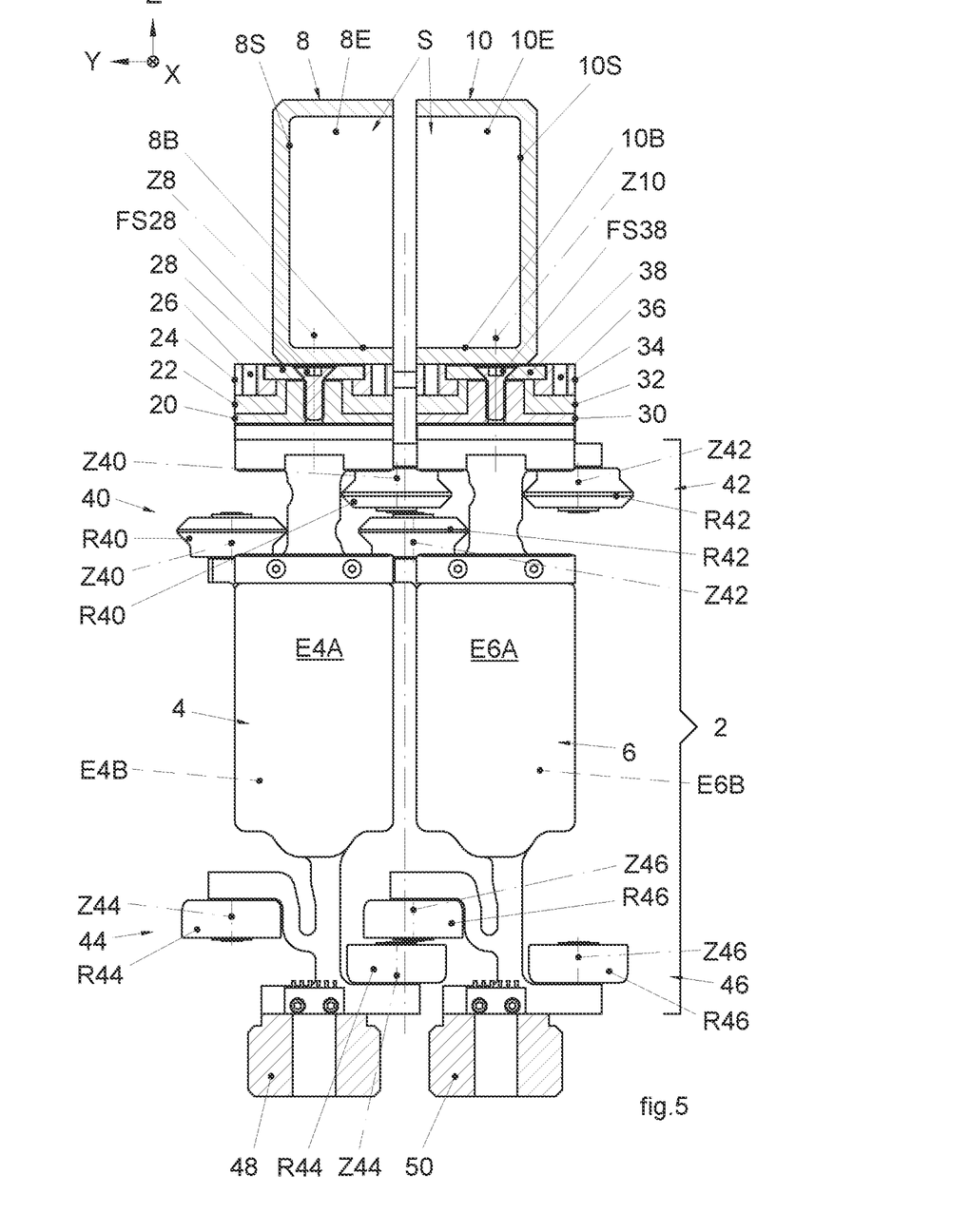
FIG. 5 is a sectional view according to the plane V-V in FIG. 4.
Figure 6:
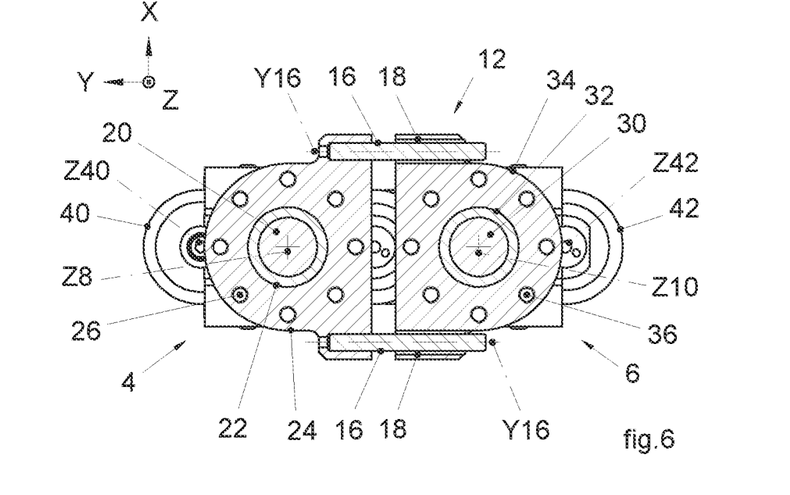
FIG. 6 is a sectional view according to the plane VI-VI in FIG. 3.

Reference number 1 in FIGS. 3 and 4 designates as a whole a carrier for a transfer system comprising a transfer path.

The carrier unit 1 comprises a pair 2 of carriers (or, better put, a paired arrangement of carriers) comprising a first carrier 4 and a second carrier 4, both individually engageable on a portion of the transfer path and configured for negotiating the transfer path itself. The carriers 4 and 6 are preferably embodied as flexible, electromagnetic driven carriers such as those known under the commercial name ACOPOSTrak®. At any rate, the carriers 4 and 6 may be embodied by other, more conventional, carriers such as mechanically engageable and driven carriers.

The first carrier 4 is coupled to a first gripper 8 configured for cooperating with a second gripper 10 coupled to the second carrier 6 to define a socket S for holding one or more products to be carried through at least part of the transfer path.

More in detail, each of the grippers 8, 10 is provided as an essentially box-shaped member each including:
- a side wall 8S, 10S
- a top wall 8T, 10T
- a bottom wall 8B, 10B
- an end wall 8E, 10E whereby when the grippers 8, 10 are set alongside one another the side walls 8S, 10S face one another and the end walls 8E, 10E, as well as the top and bottom walls 8T, 10T and 8B, 10B are substantially arranged coplanar to one another to define the socket S.

In general, the socket S has a socket geometry determined by a relative position of the first gripper 8 with respect to the second gripper 10. The socket geometry is susceptible of variation as a function of the relative position of the first and second gripper 8, 10 with respect to one another and the relative position of each gripper 8, 10 with respect to the carrier 4, 6.

More specifically, according to the invention (directions mentioned in the following are referred to a right hand reference system X-Y-Z represented in each of FIGS. 3-11):
- the first gripper 8 is rotatably coupled to the first carrier 4 around a respective first axis of rotation Z8, whereby the relative position of the first gripper 8 with respect to the first carrier 4 is defined by a first angle A8 (FIG. 10) between the first gripper 8 and the first carrier 4 around the first axis of rotation Z8,
- the second gripper 10 is rotatably coupled to the second carrier 6 around a respective second axis of rotation Z10, whereby the relative position of the second gripper 10 with respect to the second carrier 6 is defined by a second angle A10 (FIG. 10) between the second gripper 10 and the second carrier 6 around the second axis of rotation Z10,
- each carrier unit 1 comprises an angle control device 12 (which will be extensively detailed in the following) configured for adjusting the first angle A8 and the second angle A10 to maintain a predetermined socket geometry upon negotiation of a transfer path by the carrier unit 1.

With reference to FIGS. 3-7, in preferred embodiments the angle control device 12 comprises a sliding coupling between the first gripper 8 and the second gripper 10, the sliding coupling comprising a first coupling element 16 fixed to the first gripper 8 and a second coupling element 18 fixed to the second gripper 10. The first coupling element 16 is being configured to slide with respect to the second coupling element 18 in a direction Y16 transverse to the first axis Z8 and to the second axis Z10 and extending across the first axis and the second axis Z8, Z10. The number of pair of coupling elements may vary based on specific requirements, for instance for achieving better and more stable motion performances and/or dynamic performances.

In the preferred embodiment shown in the figures, the angle control device 12 for instance comprises two pairs of coupling elements 16, 18 (references A and B in parentheses reflect this) wherein:
- a first pin 16(A) and a second pin 16(B) fixed to the first gripper 8 on opposite sides of the axis Z8, the first pin and the second pin having respective longitudinal axes Y16 parallel to one another and transverse to the first axis Z8,
- a first hub 18(A) and a second hub 18(B) on opposite sides of the axis Z10 and provided on said second gripper 10, the first pin 16(A) being slidably coupled to the first hub 18(A) and the second pin 16(B) being slidably coupled to the second hub 18(B).

Each of the first pin 16(A) and the second pin 16(B) is cylindrical in shape, and is coaxially coupled, respectively, to the first hub 18(A) and the second hub 18(B) which are also cylindrical in shape. Preferably, a low-friction lining is provided inside the hub 18(A) and 18(B) to reduce friction upon sliding of the pins 16(A) and 16(B) through the hubs 18(A) and 18(B).

In alternative embodiments each of the first and second pins 16(A) and 16(B) is prismatic in shape and is shape coupled, respectively, to the first hub 18(A) and the second hub 18(B) to define a first prismatic guide and a second prismatic guide. From the stand point of available degrees of freedom in the angle control device 12, the use of cylindrical pins or prismatic pins has the same result, i.e. the sole available degree of freedom is the axial translation along direction Y16. The shape of the pins may be chosen, for instance, for structural reasons, constructional or assembly reasons, and so on.

With reference, again, to FIGS. 3 to 7, in preferred embodiments the first carrier 4 and the second carrier 6 each include a turntable assembly (T1, T2 respectively) by which rotatable coupling of the respective gripper 8, 10 to the carrier 4, 6 is achieved.

In detail, the turntable assembly T1 of the carrier 4 comprises a base plate 20 with a protruding, internally threaded hub portion, a thrust plate 22 fitted onto the hub of the base plate 20 and having itself a hub portion fitted onto the hub portion of the base plate 20 and lying flush with the protruding hub portion of the base plate 20, a rotary plate 24 fitted onto the thrust plate 22 and onto the hub portion thereof, the rotary plate 26 including a circumferential pattern of threaded bores 26 configured to be engaged by fasteners (e.g. fastening screws) FS26 which are provided for fastening the gripper 8 to the turntable 24. A closure plate 28 is fastened to the hub portion of the base plate 20 by fasteners (e.g., fastening screws FS28) to retain the turntable 24 in place and avoid axial separation thereof from the thrust plate 22 and the base plate 20. The pins 16(A), 16(B) are fixed to the turntable 24.

Similarly, the turntable assembly T2 of the carrier 6 comprises a base plate 30 with a protruding, internally threaded hub portion, a thrust plate 32 fitted onto the hub of the base plate 30 and having itself a hub portion fitted onto the hub portion of the base plate 30 and lying flush with the protruding hub portion of the base plate 30, a rotary plate 34 fitted onto the thrust plate 32 and onto the hub portion thereof, the rotary plate 36 including a circumferential pattern of threaded bores 36 configured to be engaged by fasteners (e.g. fastening screws) FS36 which are provided for fastening the gripper 10 to the turntable 34. A closure plate 38 is fastened to the hub portion of the base plate 30 by fasteners (e.g., fastening screws FS38) to retain the turntable 34 in place and avoid axial separation thereof from the thrust plate 32 and the base plate 30. The hubs 18(A), 18(B) are provided on the turntable 34, preferably integrally provided therewith.

The turntable assemblies T1, T2 including the grippers 8, 10 are mounted—respectively—onto a first and second upper roller units 40, 42, each including a staggered roller arrangement, wherein the staggering occurs along a direction parallel to the axes Z8, Z10. Specifically, the roller unit 40 is mounted onto the carrier 4 and includes a staggered pair of rollers R40, while the roller unit 42 is mounted onto the carrier 6 and includes a staggered pair of rollers R42 which partially overlaps the rollers R40 (see the two oppositely facing rollers in the mid section of the carrier unit 1).

On the opposite side of the carriers 4, 6 with respect to the roller units 40, 42 first and a second lower roller units 44, 46, each including a staggered roller arrangement, wherein the staggering occurs along a direction parallel to the axes Z8, Z10. Specifically, the roller unit 44 is mounted onto the carrier 4 and includes a staggered pair of rollers R44, while the roller unit 46 is mounted onto the carrier 6 and includes a staggered pair of rollers R46 which partially overlaps the rollers R44 (see the two oppositely facing rollers in the mid section of the carrier unit 1).

The lower roller units 44, 46 carry a respective counterweight 48, 50 to balance the weight of the turntable assemblies T1, T2 and the grippers 8, 10.

Especially in the bends, the absence of counterweights on the carriers 4, 6 may result in a tip-over of the carrier unit 1 due to the shifting of the overall centre of gravity up and out of the carriers 4, 6. In this sense, the counterweights 48, 50 reset the position of the centre of gravity to the carrier area: since engagement to the track(s) of the transfer path occurs in the area comprised between the roller units (which abut on the tracks and provide rolling support thereof, while the body of the carrier is magnetically engaged and driven by the tracks themselves), the centre of gravity has to remain in the engagement area as close as possible to the center thereof to avoid unbalancing inertial actions on the carriers.

In greater detail, each carrier 4, 6 has a first engagement portion E4A, E6A and a second engagement portion E4B, E6B opposite to the first engagement portion, whereby magnetic engagement can occur at either portion to accommodate for track changes along the transfer path (this is an inherent feature to the ACOPOSTrak® carriers). As visible in FIGS. 3 to 7, each of the first gripper 8 and the second gripper 10 is mounted on the respective carrier 4, 6 clear of the first engagement portion and the second engagement portion, and so are the turntable units T1, T2.

With reference to FIGS. 8 to 11, operation of the carrier unit 1 will now be described. The description will be provided with reference—by way of example—to a preferred application wherein the product P is a stack of diapers (baby diapers or sanitary napkins)

Figure 8:
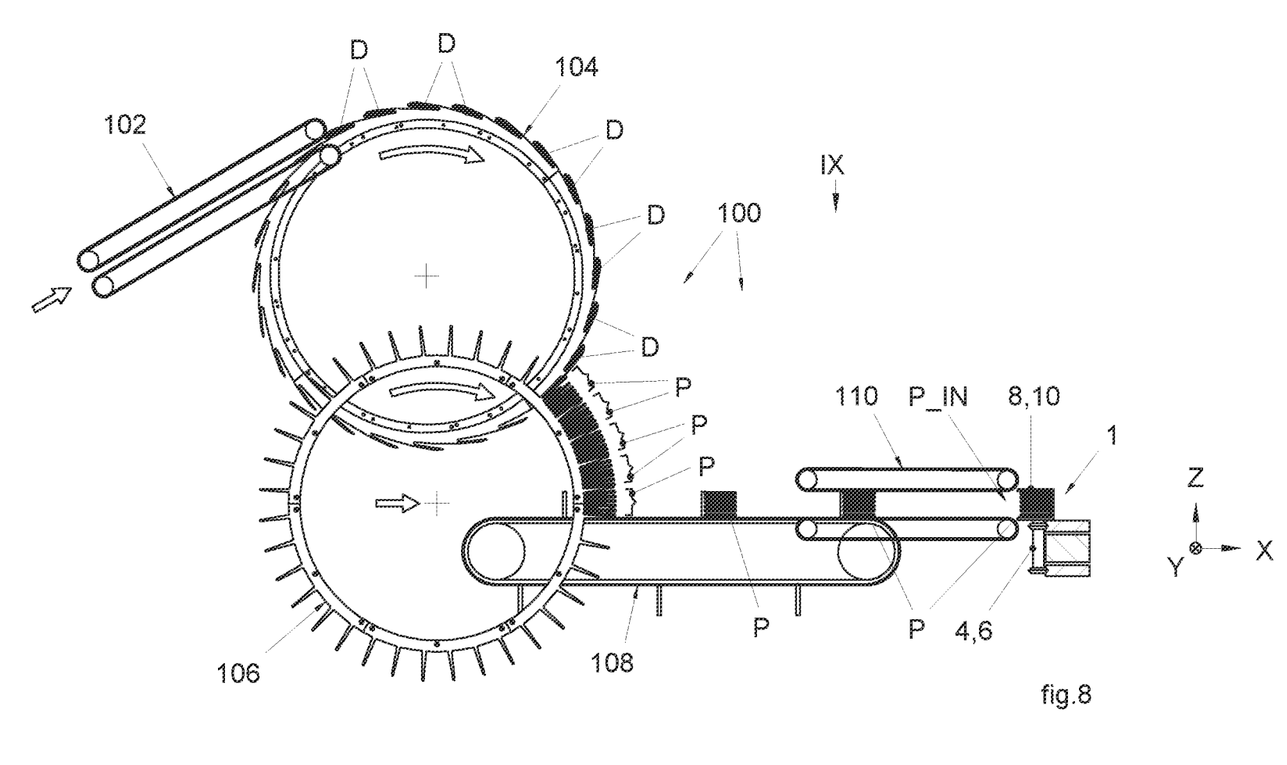
FIG. 8 represents an input station to the transfer system according to the invention, as well as a view of the transfer system itself, FIG. 9 corresponds to a plan view of the transfer system according to the invention and corresponds to the pointer IX in FIG. 8, while the pointer VIII in FIG. 9 identifies the position of the input station of FIG. 8 relative to the transfer system.
Figure 9:
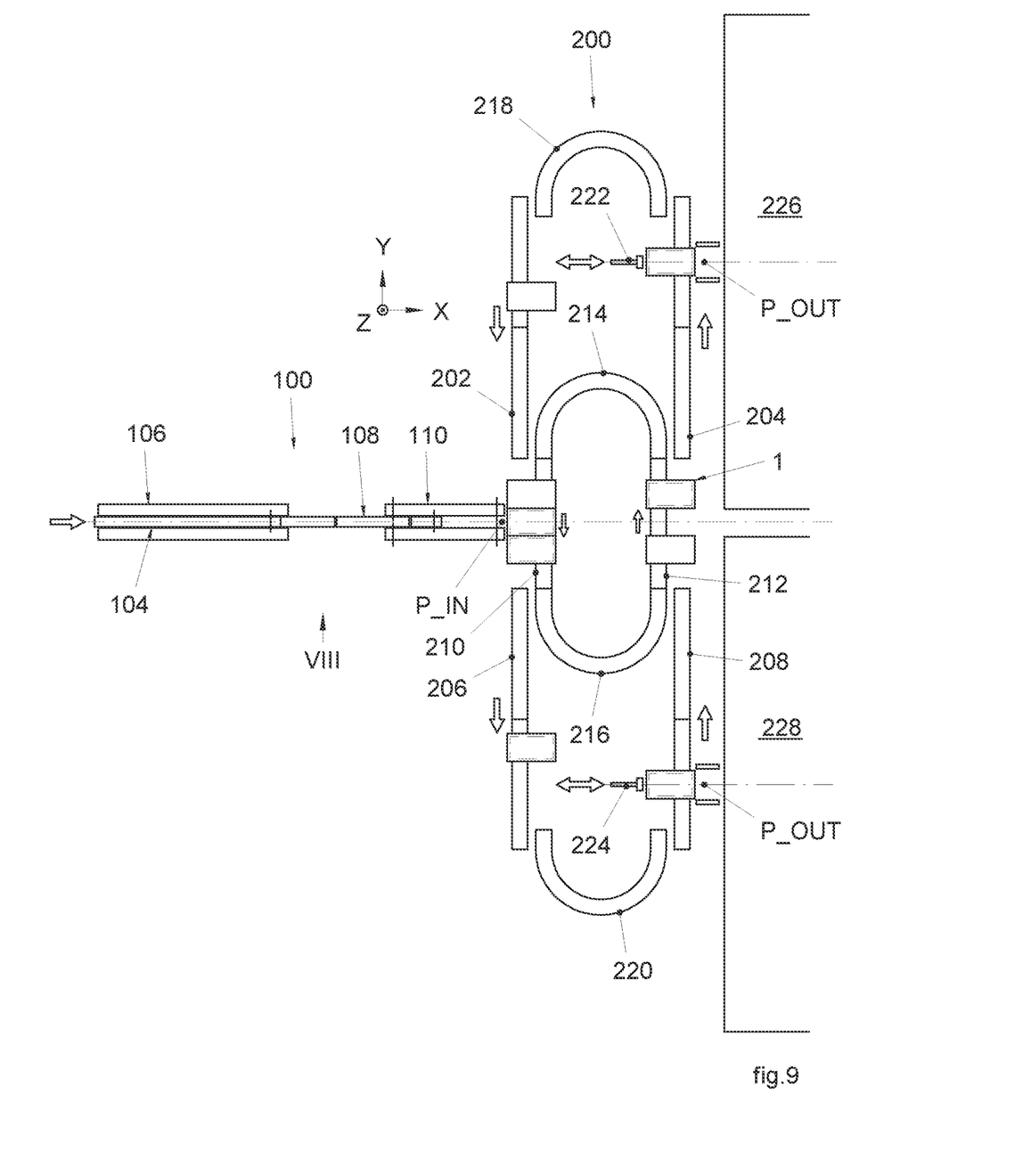

Carrier units 1 are configured to transfer products from a product input P_IN visible in FIG. 8 to one or more product output locations P_OUT visible in FIG. 9.

The product input P_IN (FIG. 8) corresponds to the location at which a carrier unit 1, so to say, takes delivery of a product P from a sorting station 100. The sorting station 100 comprises an input conveyor 102, a transfer wheel 104, a sorting wheel 106, a transfer conveyor 108 and an output conveyor 110. Any arrow reproduced on the elements above denotes a direction of motion (linear or rotational).

The input conveyor 102 receives individual diapers from upstream processing stages and delivers the same to the transfer wheel 104 (also known as "water wheel"). The transfer wheel 104 includes a plurality of vane shaped receptacles each configured for receiving and housing a diaper. The transfer wheel 104 then releases the diapers into sockets of the sorting wheel, which is configured to sort diapers into stacks defining the product P to be transferred by the carrier units 1. The sorting wheel 106 outputs the stacks of diapers onto the transfer conveyor 108, and the latter relays the products P to the output conveyor 110, which releases them to carrier units which sequentially line up at the product input P_IN.

FIG. 9 shows the position of the sorting station 100 with respect to a transfer path 200 and the product output locations P_OUT. The transfer path 200—here shown with a merely exemplary route pattern—includes an inner circle and an outer circle, the former mainly serving for buffering purposes. Each of the inner circle and the outer circle comprise straight portions and curved portions/bends.

As far as the straight portion, the outer circle comprises first and second straight portions 202, 204 on one side of the product input P_IN, and third and fourth straight portions 206, 208 on another, opposite, side of the product input P_IN. the inner circle comprises a fifth and a seventh straight portions 210, 212.

Inner bends/curved portions (U-shaped) 214, 216 connect the straight portions 210, 212 defining the inner circle, while outer bends/curved portions (U-shaped) 218, 220 connect the straight portions 202, 204 and 206, 208 respectively.

Product unloading devices 222, 224 are arranged at the product output locations P_OUT and are configured for unloading the products P from the carrier units 1 once negotiation of the transfer path from P_IN to P_OUT is completed. Product locations P_OUT correspond here to a first and a second packaging station 226, 228 whereat the products P relayed by the carrier units 1 are released by the unloading devices 222, 224.

The carrier units 1 are configured for negotiating the transfer path 200—any of the portions thereof—by magnetic engagement and driving. Of course, other driving systems and engagement systems (e.g., mechanical driving and engagement systems) may be envisaged. The paired carriers 4, 6 are driven in paired arrangement by the driving system itself both in case of electromagnetic driving such as in the ACOPOSTrak® flexible carriers, and in case of mechanical driving. Driving in paired arrangement also implies that the relative distance between the carriers 4, 6 is kept constant throughout the transfer path by the driving system itself. With electromagnetically driven carriers 4, 6 the inter-carrier distance can be adjusted by the driving system and kept constant, and can also be adjusted during travel, if required (for instance, when slowing down along rectilinear portions in the final approach to a product output location P_OUT).

Figure 7:
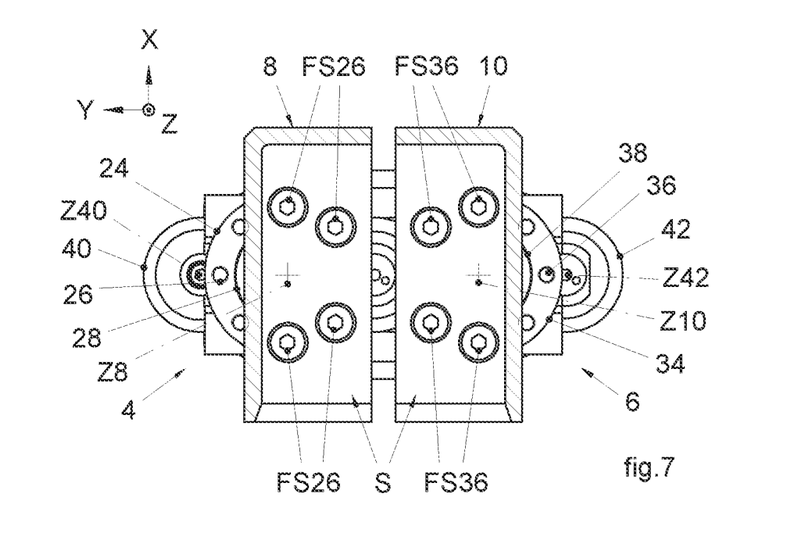
FIG. 7 is a sectional view according to the plane VII-VII in FIG. 3.
Figure 10:
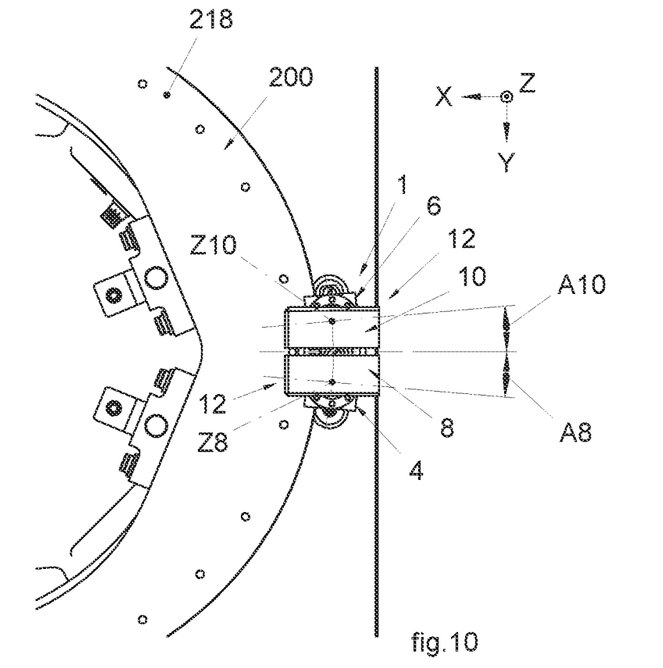
FIGS. 10 and 11 are, respectively, a plan and an elevational view of the transfer system of the invention.
Figure 11:
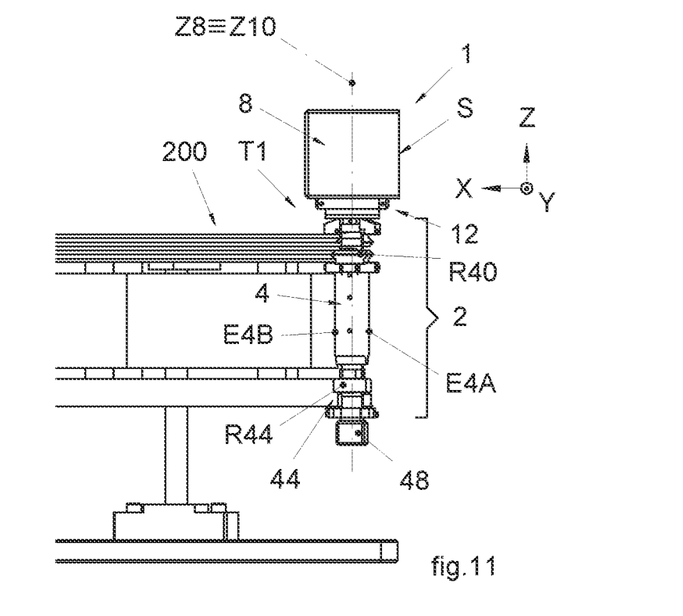

The engagement condition is visible in FIG. 11, wherein the contact between the rollers R40-R46 on the guides of the transfer path 200 is also visible. FIG. 10 in combination with FIGS. 3 and 7 shows the operation and the effect of the angle control device 12.

In prior art systems such as those in FIGS. 1 and 2 the rigid connection between the grippers and the respective carriers results in the gripper following the carrier motion when the latter negotiates a bend. As a result, the gripper tends to "open up" and diverge because of the negotiation of a bend such as that visible in FIGS. 1 and 2. In other words, the socket geometry is completely disrupted, as the relative position between the gripper changes during negotiation of the bend.

Thanks to the angle control device 12, the relative position between the grippers 8, 10 is continuously controlled during negotiation of a bend to maintain the predetermined, pre-set socket geometry (i.e., the geometry of the socket S). More in detail, the angle control device 12 adjusts the angle between the gripper 8, 10 and the carrier 4, 6 to maintain a constant socket geometry: this is done through the sliding coupling of the two grippers through the pin-hub pairs 16(A)-18(A) and 16(B)-18(B). as said, the sole available degree of freedom for the grippers 8, 10 is the relative motion in the direction Y16, but the relative rotation, as well as any other type of relative displacement, is prevented from the double constraint provided by the pin-hub engagement (the same can be obtained by a single pin-hub engagement, only provided as a prismatic guide).

Once the desired socket geometry—for example the socket width determined by the distance between walls 8S-10S —is set by fixing the distance between the carriers 4, 6 (this can be done as a standard features on transfer system using flexible carriers such as the ACOPOSTrak® carriers, as well as on fully mechanical systems), the socket geometry is maintained thanks to the sliding coupling between the grippers 8, 10 which automatically adjusts the gripper-carrier angle: as the grippers 8, 10 cannot rotate relative to one another due to the sliding coupling 16-18 (16(A)-18(A) and 16(B)-18(B)), the carriers 4, 6 rotate relative to the grippers 8, 10 (better put, they rotate "under" the grippers 8, 10) owing to the turntable units T1, T2, so that the carriers can adapt to and negotiate the transfer path 200 while the grippers are bound to one another by the sliding coupling. The angle between the grippers remains constant and equal to zero degrees, and so does the geometry of the socket S as the relative distance of the grippers 8, 10, hence of the inner side walls 8S, 10S, does not vary, while the angles A8 and A10 are continuously adjusted as a function of the radius of curvature, i.e., based on the features of the transfer path that are negotiated by the carrier unit 1. The angle control device 12 determines the amount of the angles A8 and A10 based on the preset geometry of the socket S and the radius of curvature. Such angles constitute sort of mechanical compensation between two different boundary (and driving) conditions: the shape of the transfer path (radius of curvature) and the geometry of the socket S.

Note also that angles A8 and A10 can instantaneously be different: the radius of curvature along the bends 214-220 may vary through the bend, whereby the leading carrier 4 or 6 may momentarily be located at a section of the bend with a different radius of curvature than the trailing carrier 6 or 4.

Maintaining a predetermined socket geometry according to the invention also includes maintaining a predetermined socket dimension that varies according to a predetermined law or pattern, while maintaining the angle between the grippers 8, 10 at a zero value. For instance, while keeping the side walls 8S, 10S parallel to one another thanks to the angle control device 12, the inter-gripper distance along the direction Y may be varied according to a predetermined pattern (this, as indicated in the foregoing, can be easily achieved by electromagnetically driven carriers 4, 6) while the angles A8 and A10 are continuously adjusted (in either direction) to accommodate—in combination—the mechanical constraint set up by the angle control device 12, the radius of curvature of the transfer path and the inter-gripper distance.

Additionally, in alternative embodiments the angle control device 12 may not be based on a mechanical coupling, but is may rather comprise a first drive unit configured for controlling the first angle A8 and a second drive unit configured for controlling the second angle A10. The first drive unit and the second drive unit may comprise an electric motor configured for driving the turntable unit T1, T2. The drive units may be controlled by a transfer system control unit which, based on the preset geometry of the socket S and the position of the carrier 4, 6 along the transfer path 200 (the position is associated i.a. to a radius of curvature) determines the required value of the angles A8 and A10 to maintain the desired geometry of the socket S, thereby obtaining the same effect on the geometry of the socket S as the sliding coupling between pins 16 and hubs 18.

Figure 12:
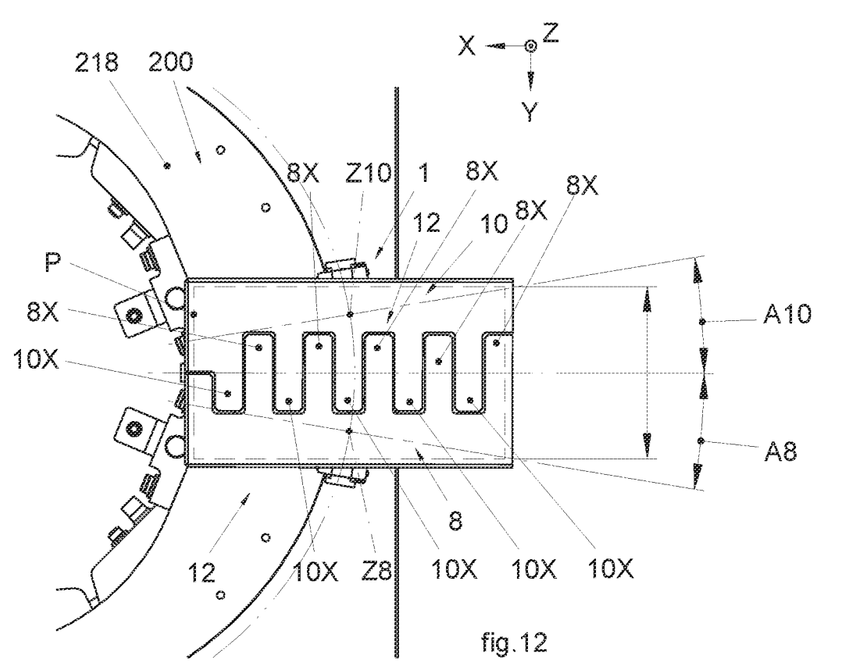
FIG. 12 is a plan view of a carrier unit according to further embodiments of the invention.

With reference to FIG. 12, in yet further embodiments of the invention the shape of the grippers 8, 10 may be modified to incorporate comb-like extensions 8X, 10X of the top walls 8T, 10T and/or the bottom walls 8B, 10B (the "and" alternative is preferred) and are configured to interdigitate to a variable extent—depending on the socket geometry—with the comb-like extensions of the other gripper as shown in FIG. 12. More in general, the comb-like extensions may be provided on any individual pair of walls of the grippers 8, 10 that are set alongside one another when the grippers are positioned to define the socket S: this includes the top walls 8T, 10T, the bottom walls 8B, 10B, but also the end walls 8E, 10E. the comb-like extensions 8X, 10X may be provided on any of these pairs alone or in combination with the others.

These specific embodiments provide at least two key technical advantages, namely:

first and foremost, the arrays of comb-like extensions 8X, 10X embody the angle control device 12, as the interdigitation of the extensions 8X, 10X allows the same degrees of freedom in the relative motion between the grippers 8, 10 as the pins 16 sliding through the hubs 18. Note in this respect that the only relative motion allowed for the grippers 8, 10 by the extensions 8X, 10X is a sliding motion along a direction which is overall parallel to the axes Y16 of the pins 16. This simplifies the construction of the carriers 4, 6 as the structural and geometric features required, for instance, to implement the pin-hub pairs 16, 18 or to accommodate the drive units can be actually dispensed with, thereby relying on the very grippers to provide the very angle control device 12 therefor;

second, the extensions 8X, 10X globally bestow the socket S with full enclosure features regardless of the socket geometry. In other words, the interdigitation between the extensions 8X, 10X prevents the formation of a continuous gap (of course net of the operational plays) between the grippers 8, 10 throughout all the socket geometry range allowed by the length of the extensions 8X, 10X in the sliding direction. Maintenance of the geometry of the socket S is therefore achieved throughout all of the transfer path 200, whereby multiple transfer patterns can be implemented therethrough without any of the technical problems affecting the prior art. The transfer system may operate at maximum speed even in the bends because the interference condition determined by the geometry of the socket S will not change from a straight portion to a curved/bend portion thanks to the angle control device 12.

It is noted, however, that the embodiments of FIG. 12 may also be practised with an angle control device 12 combining the arrays of comb-like extensions 8X, 10X with the pairs of coupling elements 16A, 16B and 18A, 18B (pins and hubs—whether cylindrical or prismatic in shape) as disclosed in respect of the embodiments of FIGS. 3 to 11, as well as with an angle control device 12 combining the arrays of comb-like extensions 8X, 10X with the first drive unit configured for controlling the first angle A8 and the second drive unit configured for controlling the second angle A10. As disclosed in the foregoing, such first drive unit and the second drive unit may comprise an electric motor configured for driving the turntable unit T1, T2.

Naturally, while the principle of the invention remains the same, the details of construction and the embodiments may widely vary with respect to what has been described and illustrated purely by way of example, without departing from the scope of the present invention.

The invention claimed is:

1. A carrier unit for a transfer system having a transfer path, the carrier unit comprising:
   a first carrier and a second carrier, the first and the second carriers being engageable to the transfer path and configured for negotiating the transfer path, wherein the first carrier is coupled to a first gripper configured for cooperating with a second gripper coupled to the second carrier to define a socket for holding one or more products, the socket having a socket geometry determined by a relative position of the first gripper with respect to the second gripper, and
   first and second turntable assemblies rotatably coupling the respective first and second grippers to the respective first and second carriers,
   wherein:
   the first gripper is rotatably coupled to the first carrier around a respective first axis of rotation, whereby the relative position of the first gripper with respect to the first carrier is defined by a first angle between the first gripper and the first carrier around the first axis of rotation,
   the second gripper is rotatably coupled to the second carrier around a respective second axis of rotation, whereby the relative position of the second gripper with respect to the second carrier is defined by a second angle between the second gripper and the second carrier around the second axis of rotation, and
   each carrier unit comprises an angle control device configured for adjusting the first angle and the second angle to maintain a predetermined socket geometry upon negotiation of the transfer path by the carrier unit, wherein the angle control device comprises arrays of comb-like extensions of top walls and/or bottom walls of the first and second grippers, the comb-like extensions of one of the first and second grippers being configured to interdigitate with the comb-like extensions of the other of the first and second grippers, and
   the first and second turntable assemblies each include respective first and second:
   base plates coupling the respective first and turntable assemblies to the respective first and second carriers, each base plate including a protruding hub;
   thrust plates coupled to the base plates, including about the protruding hubs;
   rotary plates rotationally fitted onto the thrust plates and coupled to the respective first and second grippers; and
   closure plates coupled to the base plate and configured to retain the respective turntable assemblies in place and prevent axial separation of components of the turntable assemblies in a direction parallel to the first and second axes of rotation, which are each parallel to a longitudinal axis of each carrier unit.

2. The carrier unit of claim 1, wherein the angle control device comprises a sliding coupling between the first gripper and the second gripper, the sliding coupling comprising a first coupling element fixed to the first gripper and a second coupling element fixed to the second gripper, the first coupling element being configured to slide with respect to the second coupling element in a direction transverse to the first axis of rotation and to the second axis of rotation and extending across the first axis of rotation and the second axis of rotation.

3. The carrier unit of claim 1, wherein said angle control device comprises:
   a first pin and a second pin fixed to said first gripper, the first pin and the second pin having respective longitudinal axes parallel to one another and transverse to the first axis of rotation, the longitudinal axes being arranged on opposite sides of the first axis of rotation, and
   a first hub and a second hub provided on said second gripper, the first pin being slidably coupled to said first hub and the second pin being slidably coupled to said second hub, the first hub and the second hub being arranged on opposite sides of the second axis of rotation.

4. The carrier unit of claim 3, wherein each of the first pin and the second pin is cylindrical in shape, and is coaxially coupled, respectively, to the first hub and the second hub which are also cylindrical in shape.

5. The carrier unit of claim 3, wherein each of the first pin and the second pin is prismatic in shape and is shape coupled, respectively, to the first hub and the second hub to define a first prismatic guide and a second prismatic guide.

6. The carrier unit of claim 1, wherein the angle control device comprises a first drive unit configured for controlling the first angle and a second drive unit configured for controlling the second angle.

7. The carrier unit of claim 6, wherein the first drive unit and the second drive unit comprise an electric motor.

8. The carrier unit of claim 1, wherein the predetermined socket geometry includes a socket width defined as the distance between facing inner walls of the first gripper and the second gripper along a direction transverse to the first axis of rotation and the second axis of rotation, and extending across them.

9. The carrier unit of claim 8, wherein the predetermined socket geometry comprises a predetermined socket width.

10. The carrier unit of claim 1, wherein each of the first and second carriers is configured for magnetic engagement to the transfer path.

11. The carrier unit of claim 1, wherein:
    the protruding hub of each base plate includes an internally threaded bore and an uppermost surface;
    each transfer plate includes a protruding hub, which is fitted about the respective protruding hubs of each base plate, the protruding hub of each thrust plate having an uppermost surface configured to be flush with the uppermost surface of the respective base plate; and
    each closure plate includes an externally threaded hub protruding in an opposite direction as the protruding hubs of the base plates and thrust plates, the externally threaded hub configured to be fastened to the internally threaded bore of the protruding hubs of the base plates.

12. The carrier unit of claim 1, further comprising first and second roller units respectively coupling the first and second turntable assemblies to the respective first and second carriers.

13. The carrier unit of claim 12, wherein:
each of the first and second roller units includes respective first and second pairs of rollers, each pair of rollers being staggered relative to the respective first and second axes of rotation;
the first roller unit being spaced apart from the second roller unit along the longitudinal axis; and
the first roller unit overlaps the second roller unit in a direction perpendicular to the longitudinal axis.

14. A transfer system comprising a transfer path and one or more carrier units according to claim 1, each of the one or more carrier units being configured to engage and negotiate portions of the transfer path to transfer the products carried thereby along the transfer path.

\* \* \* \* \*

UNITED STATES PATENT AND TRADEMARK OFFICE
CERTIFICATE OF CORRECTION

| | | |
|---|---|---|
| PATENT NO. | : 12,193,918 B2 | Page 1 of 1 |
| APPLICATION NO. | : 17/737171 | |
| DATED | : January 14, 2025 | |
| INVENTOR(S) | : Gabriele Sablone et al. | |

It is certified that error appears in the above-identified patent and that said Letters Patent is hereby corrected as shown below:

On the Title Page

Item (71) Applicant address information should be listed as:
- Fameccanica.Data S.p.A., San Giovanni Teatino (Chieti), ITALY -

Item (72) Inventor address information should be listed as:
- Gabriele SABLONE, San Giovanni Teatino (Chieti), ITALY
Massimiliano ROSSETTI, San Giovanni Teatino (Chieti), ITALY
Carlo DI SABATINO, San Giovanni Teatino (Chieti), ITALY
Marco DELLI ROCIOLI, San Giovanni Teatino (Chieti), ITALY -

Signed and Sealed this
First Day of April, 2025

Coke Morgan Stewart
*Acting Director of the United States Patent and Trademark Office*